US008623284B2

(12) United States Patent
Chakravarty et al.

(10) Patent No.: US 8,623,284 B2
(45) Date of Patent: *Jan. 7, 2014

(54) PHOTONIC CRYSTAL MICROARRAY LAYOUTS FOR ENHANCED SENSITIVITY AND SPECIFICITY OF LABEL-FREE MULTIPLE ANALYTE SENSING, BIOSENSING AND DIAGNOSTIC ASSAY

(75) Inventors: Swapnajit Chakravarty, Austin, TX (US); Ray T. Chen, Austin, TX (US)

(73) Assignee: Omega Optics, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/607,793

(22) Filed: Sep. 9, 2012

(65) Prior Publication Data
US 2013/0005605 A1    Jan. 3, 2013

Related U.S. Application Data

(63) Continuation-in-part of application No. 12/462,311, filed on Aug. 3, 2009, now Pat. No. 8,293,177.

(51) Int. Cl.
*G01N 21/00*    (2006.01)

(52) U.S. Cl.
USPC ............... 422/82.11; 422/82.09; 385/12

(58) Field of Classification Search
USPC ............ 422/400, 127, 82.09, 82.11; 385/123, 385/124, 129, 132, 43, 477, 478, 480, 481
See application file for complete search history.

(56) References Cited

U.S. PATENT DOCUMENTS

2006/0072642 A1*   4/2006   Wang et al. .............. 372/50.1

OTHER PUBLICATIONS

Zou Y et al., "Methods to array photonic crystal microcavities for high throughput high sensitivity biosensing on a silicon-chip based platform", Lab Chip 12, 2309 (2012).
Lai W-C. et al., "Silicon nano-membrane based photonic crystal microcavities for high sensitivity bio-sensing", Optics Lett. 37(7), 1208 (2012).
Chakravarty S. et al., "Slow light engineering for high Q high sensitivity photonic crystal microcavity biosensors in silicon", Biosens. Bioelectron. 38(1), 170 (2012).

* cited by examiner

*Primary Examiner* — Natalia Levkovich
(74) *Attorney, Agent, or Firm* — Taboada Law Firm, PLLC; John M. Taboada

(57) ABSTRACT

Methods and systems for label-free multiple analyte sensing, biosensing and diagnostic assay chips consisting of an array of photonic crystal microcavities along a single photonic crystal waveguide are disclosed. The invention comprises an on-chip integrated microarray device that enables detection and identification of multiple species to be performed simultaneously using optical techniques leading to a high throughput device for chemical sensing, biosensing and medical diagnostics. Other embodiments are described and claimed.

15 Claims, 16 Drawing Sheets

PHOTONIC CRYSTAL MICROARRAY LAYOUTS FOR ENHANCED SENSITIVITY AND SPECIFICITY OF LABEL-FREE MULTIPLE ANALYTE SENSING, BIOSENSING AND DIAGNOSTIC ASSAY

I. CROSS REFERENCE TO RELATED APPLICATIONS

The application is a continuation-in-part application of U.S. patent application Ser. No. 12/462,311, titled "Photonic Crystal Microarray Device for Label-Free Multiple Analyte Sensing, Biosensing and Diagnostic Assay Chips", filed Aug. 3, 2009, the contents of which are hereby incorporated by reference.

II. BACKGROUND

1. Field of the Invention

This invention relates generally to the field of optical and medical devices, and more specifically to an apparatus and method for microarray implementation for the detection of multiple analytes such as chemical agents and biological molecules using photonic crystals.

2. Background of the Invention

Label-free optical sensors based on photonic crystals have been demonstrated as a highly sensitive potential method for performing a large range of biochemical and cell-based assays. For background information on photonic crystals, the reader is directed to Joannopoulos, J. D., R. D. Meade, and J. N. Winn, *Photonic Crystals,* 1995 Princeton, N.J.: Princeton University Press. Tight confinement of the optical field in photonic crystal microcavities leads to a strong interaction with the surrounding ambient in the vicinity of the microcavity, thereby leading to large sensitivity to changes in refractive index of the ambient. Much of the research in photonic crystal devices has relied on enhancing refractive index sensitivity to a single analyte (Lee M. R., Fauchet M., "Nanoscale microcavity sensor for single particle detection," Optics Letters 32, 3284 (2007)). Research on photonic crystals for multiple analyte sensing has focused on one-dimensional photonic crystal grating-like structures (see patents US20080225293 and US20030027328) that measure the resonant peak reflected wavelengths; such sensors have wide linewidths of the resonant peaks due to one-dimensional confinement and do not utilize the full potential of narrow resonant linewidths of two-dimensional photonic crystal microcavities. Furthermore, measurements are made from each sensor element in the array in a serial process, requiring multiple sources and detectors for parallel sensing beyond a single element. Research has been performed with one-dimensional photonic crystal microcavities coupled to ridge waveguides (See Mandal S. and Erickson D., "Nanoscale optofluidic sensor arrays", Optics Express 16, 1623 (2008)). One dimensional photonic crystal microcavities, in addition to poor optical confinement, do not utilize the slow light effect due to reduced group velocity in two-dimensional photonic crystal waveguides that would otherwise enhance coupling efficiency and thereby improve signal-to-noise ratio of sensing. Demonstrated two dimensional photonic crystal waveguide biosensors rely on shifts of the stop-gap (see Skivesen N. et al., "Photonic crystal waveguide biosensor", Optics Express 15, 3169 (2007)) or shifts of the resonant peak of an isolated microcavity (see Chakravarty S. et al., "Ion detection with photonic crystal microcavities", Optics Letters 30, 2578 (2005)). In either case, the design is not suitable for the fabrication of microarrays for multiple analyte sensing.

Two dimensional photonic crystal microcavities integrated with two-dimensional photonic crystal waveguides offer the possibility of integrating the high quality-factor resonances of two-dimensional photonic crystal microcavities with the slow light effect of two-dimensional photonic crystal waveguides for high sensitivity, high signal-to-noise ratio sensing. Furthermore, multiple photonic crystal microcavities can be simultaneously arrayed along a single photonic crystal waveguide, so that a single measurement can be performed in parallel to elicit the response from multiple sensor elements, thereby increasing measurement throughput and reducing cost. An array of two sensors demonstrated using two-dimensional photonic crystal microcavities uses multiple ridge waveguides between individual photonic crystal microcavities. Coupling between photonic crystal waveguides and ridge waveguides introduces additional significant transmission loss at each interface, thereby significantly reducing signal-to-noise ratio as each microcavity is added for multiple sensing. The design demonstrated by Guillermain et al. (see Guillermain E., Fauchet P. M., "Multichannel sensing with resonant microcavities coupled to a photonic crystal waveguide," JWA 45, CLEO Conference (2009)) in effect employs multiple photonic crystal waveguides and also employs microcavities with significantly poor quality factors that make the designs unsuitable for high sensitivity sensing. Better designs are needed in the art to realize photonic crystal microarray devices that efficiently couple light from ridge waveguides to a single photonic crystal waveguide, wherein multiple photonic crystal microcavities with high quality factors and covering a large bandwidth for sensing are coupled to a single photonic crystal waveguide for high sensitivity multiple sensing.

A standard on-chip multiple protein patterning technique using lithography typically requires a pre-bake resist temperature of 100° C. or higher. At the very least, temperatures this high compromise or alter biological functionality, and at the very worst they may destroy its function. Most proteins are stable in vivo at a temperature of 37° C., but this stability is dependent on chaperone proteins that maintain the proper conformation of other proteins in cells. Since proteins in vitro lack these chaperone proteins, they must be maintained at even lower temperatures to prevent denaturation and loss of function. Designs are needed to enable patterning of different kinds of biomolecules in aqueous phase to preserve functionality of biomolecules.

Designs are needed in the art to integrate two-dimensional photonic crystal microcavities with two-dimensional photonic crystal waveguides for multiple analyte sensing and designs are further needed to pattern multiple biomolecules, of different constitutions, on the photonic crystal substrate while preserving their functionality.

III. SUMMARY

One embodiment of the invention provides a sensor comprising a semiconductor material core with high dielectric constant, supported on the bottom by a low dielectric constant cladding. A triangular lattice of photonic crystal holes is etched into the substrate. The photonic crystal waveguide is defined by filling a single row of holes, from input ridge waveguide transition to output ridge waveguide transition with the semiconductor core material. A photonic crystal microcavity is similarly defined by filing a few holes with semiconductor core material. Multiple photonic crystal microcavities are patterned at a distance of three lattice constants from the photonic crystal waveguide. The distance between individual photonic crystal microcavities is 10 lattice periods. The high dielectric constant core with structured photonic crystal waveguide and photonic crystal microcavities, together with the low dielectric constant cladding, form the photonic crystal microarray structure. Light is coupled into the photonic crystal waveguide from a ridge waveguide. Light is out-coupled from the photonic crystal waveguide to an output ridge waveguide. When a broadband light source is input to the photonic crystal waveguide, wavelengths corresponding to the resonant wavelengths of the individual microcavities are coupled to the corresponding microcavities. As a result, minima are observed in the transmission spectrum corresponding to the dropped wavelength of each photonic crystal microcavity. Depending upon the wavelength range of interrogation, the period of the sub-wavelength lattice can vary from 50 nm to 1500 nm and the depth of the lattice structure can vary from 0.4 to 0.7 times the lattice periodicity above. The semiconductor material can be silicon (or any Group IV material), gallium arsenide (or any III-V semiconductor) or any semiconductor material with high refractive index. The substrate can be any Group IV material corresponding to the Group IV core material, or any substrate suitable to grow the III-V core material. Above the microcavity, a thin film of target binding molecules that are immobilized on the microcavity surfaces, each microcavity surface being coated with an exclusive target molecule or biomolecule, forms the dielectric coating. The one or more binding molecules are free of detection labels. The one or more specific binding substances are thus arranged in an array on the microcavities, along the photonic crystal waveguide. A single transmission spectrum therefore probes the binding events on multiple microcavities. A binding event on a specific microcavity shifts the corresponding transmission minimum and leads to a sensing event for the specific microcavity. Analyzed biomolecules can be proteins, DNA, RNA, small molecules or genes. Arrays of microcavities therefore lead to a multiple analyte sensing device that increases the measurement throughput of the device, in addition to the obvious sensitivity enhancements achieved by using a two-dimensional photonic crystal waveguide coupled to two-dimensional photonic crystal microcavities.

To summarize:

The primary objective of the invention is to provide an integrated photonic crystal microarray with compact size that can be monolithically integrated with different kinds of biomolecules such as proteins, nucleic acids, DNA, RNA or small molecules to implement a personalized diagnostic chip.

The second objective of the invention is to eliminate the need for labeling of biomolecule and biomolecule conjugates for on-chip detection and thereby reduce microarray costs associated with biomolecule labeling.

The third objective of the invention is to significantly increase measurement throughput from devices by signal collection and analysis from multiple elements of a microarray in a single measurement as opposed to individual element measurement in contemporary systems.

The fourth objective of the invention is to implement a novel lithography scheme on a CMOS chip that avoids high temperature processes associated with photolithography and chemical etching for the patterning of multiple biomolecules and thereby preserves biomolecule functionality in aqueous phase at room temperatures or even colder if necessary.

Other objectives and advantages of the present invention will become apparent from the following descriptions, taken in connection with the accompanying drawings, wherein, by way of illustration and example, an embodiment of the present invention is disclosed.

IV. BRIEF DESCRIPTION OF THE DRAWINGS

The drawings constitute a part of this specification and include exemplary embodiments of the present invention, which may be embodied in various forms. It is to be understood that in some instances various aspects of the present invention may be shown exaggerated or enlarged to facilitate an understanding of the invention.

A more complete and thorough understanding of the present invention and benefits thereof may be acquired by referring to the following description together with the accompanying drawings, in which like reference numbers indicate like features, and wherein:

FIG. 1A is a top view of one embodiment of a photonic crystal microarray device based on an array of N photonic crystal microcavities coupled to a photonic crystal waveguide. In FIG. 1A, N is chosen arbitrarily as 4 for space constraints. FIG. 1B is an enlarged section of FIG. 1A.

Figure 7A:
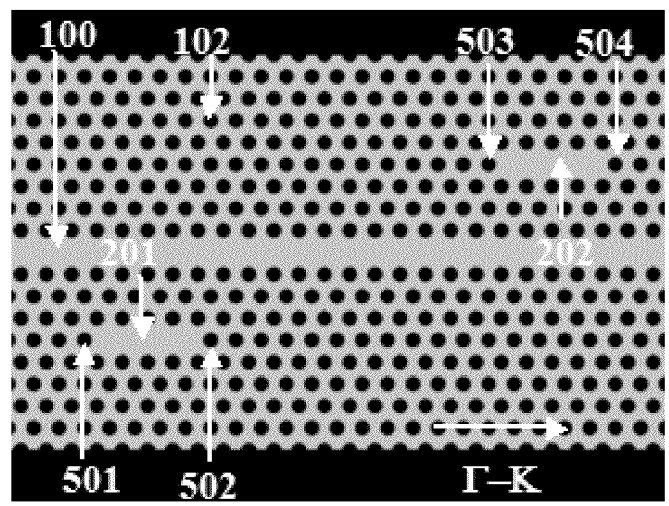
Figure 7B:
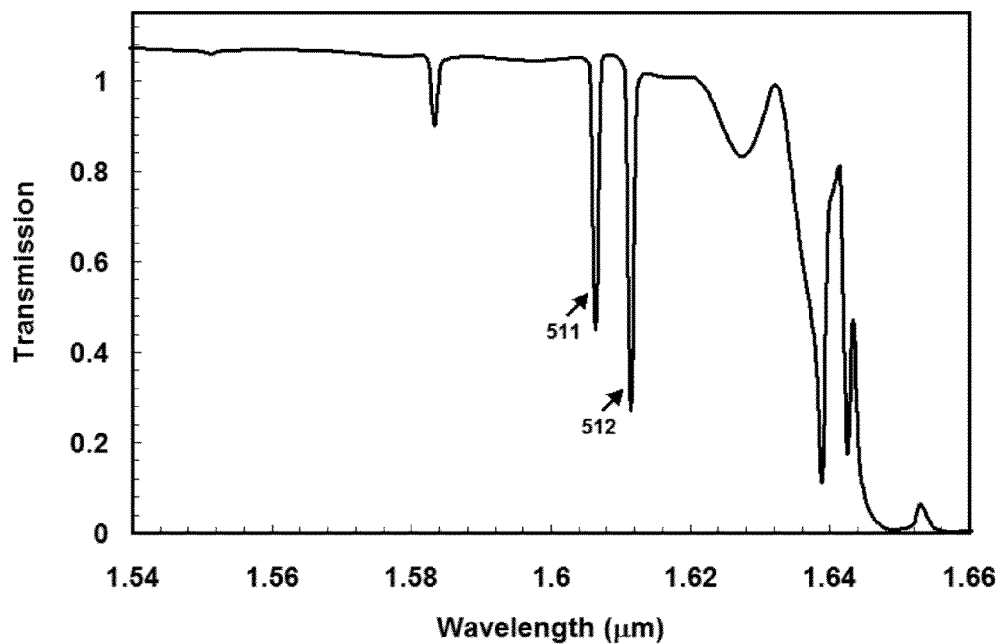

FIG. 7A shows a top view of a functional photonic crystal waveguide with two representatively coupled photonic crystal microcavities along the length of the photonic crystal waveguide. Two (2) microcavities are chosen, as a representative number for n. n can vary from 1 to N (N→∞). FIG. 7B shows the transmission spectrum of the embodiment depicted in FIG. 7A.

Figure 8A:
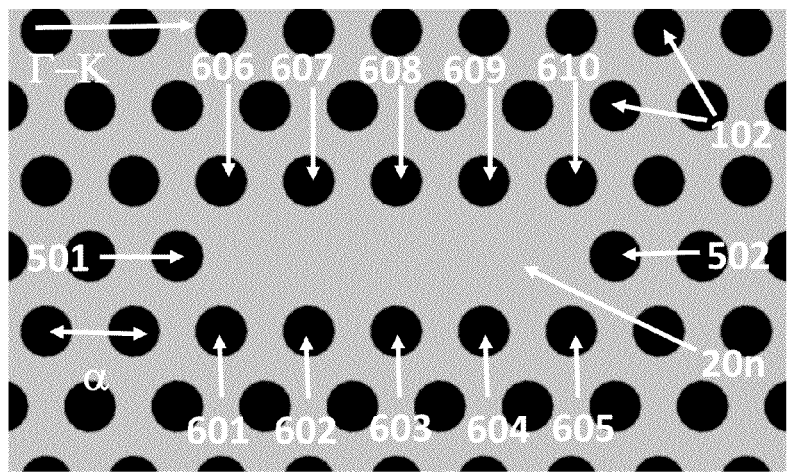
Figure 8B:
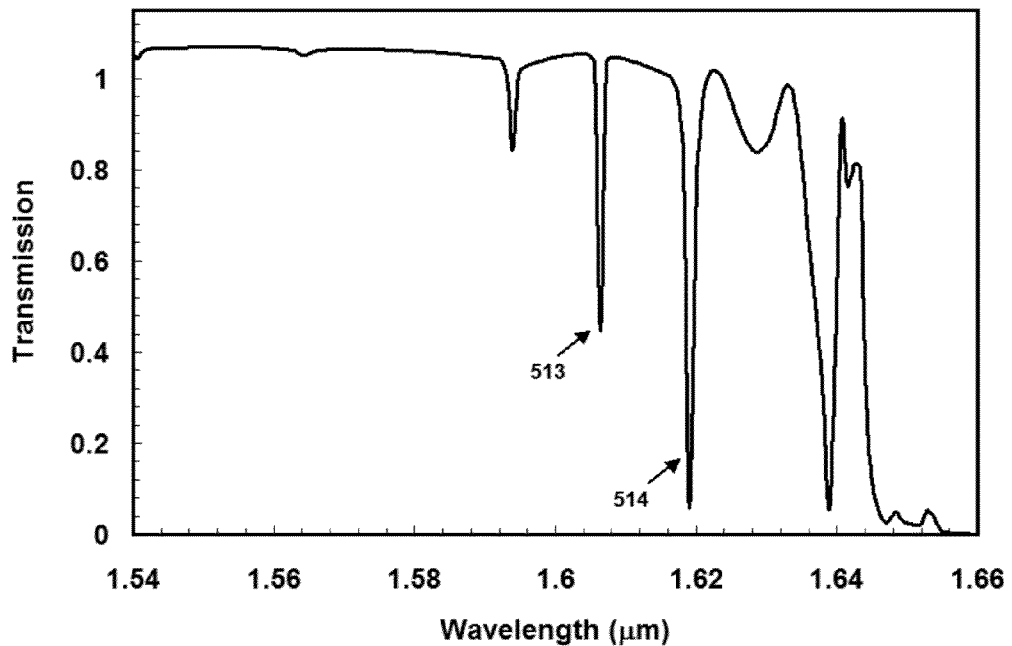
Figure 8C:
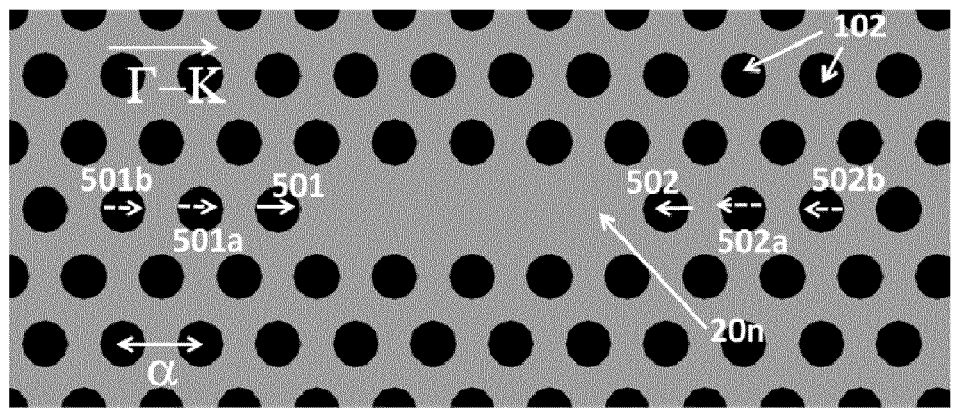
Figure 8D:
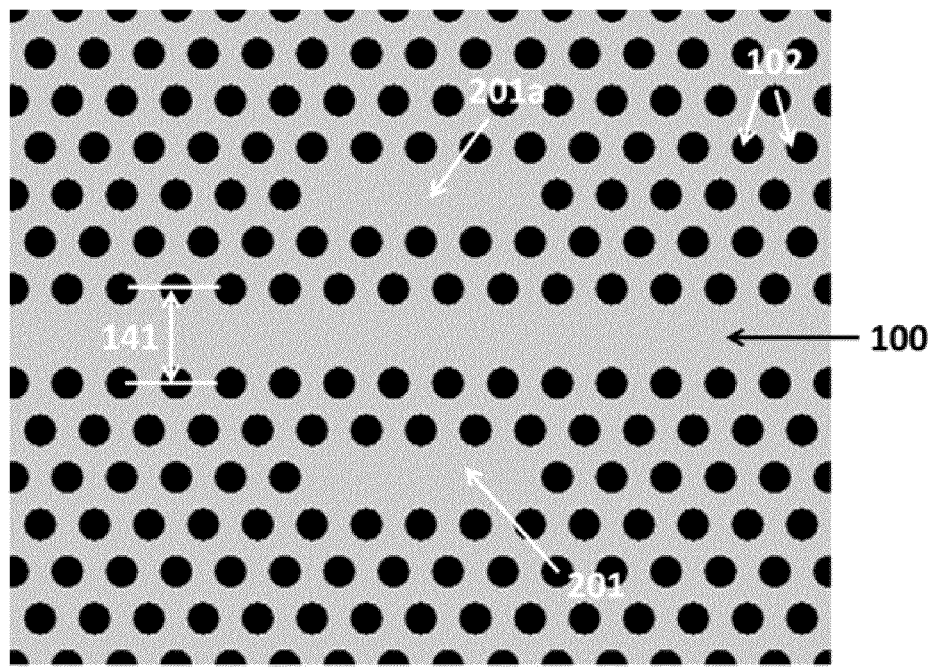
Figure 8E:
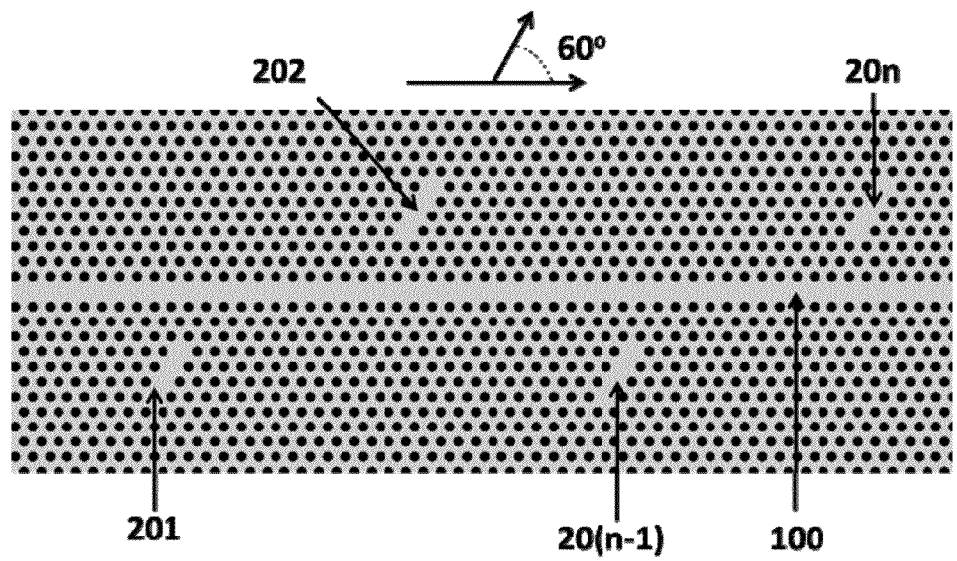
Figure 8F:
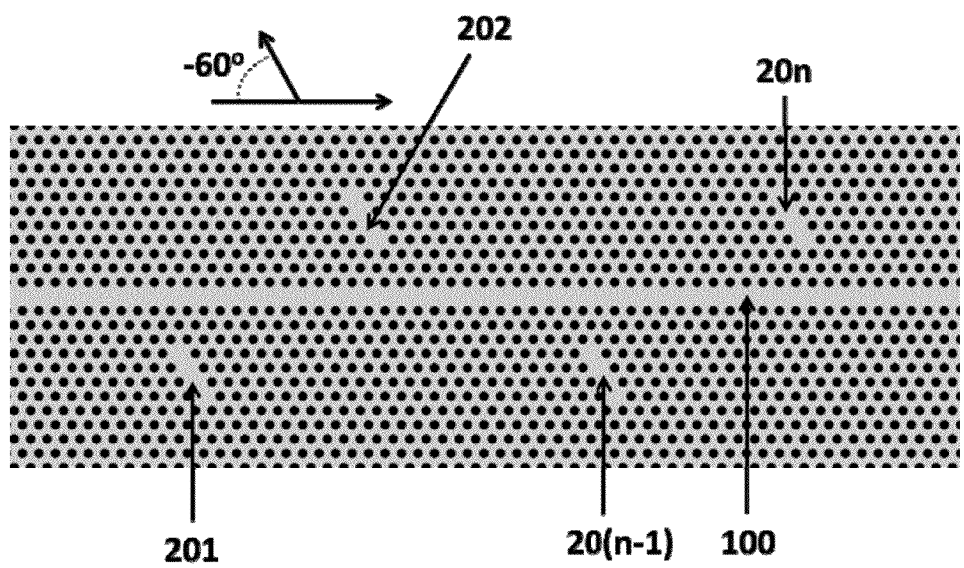

FIG. 8A shows a top view of a functional photonic crystal microcavity. Elements that are geometrically tuned in size and/or position are indicated. FIG. 8B shows the transmission spectrum when two representative photonic crystal microcavities of the embodiment depicted in FIG. 8A are coupled to the functional photonic crystal waveguide in FIG. 1A and FIG. 1B. FIG. 8C shows a top view of a functional photonic crystal microcavity where more than just the adjacent void columnar members have been shifted. FIG. 8D shows a top view of a composite microcavity comprising two mirrored functional photonic crystal microcavities. FIG. 8E shows a top view of functional photonic crystal microcavities oriented along the +60 degrees orientation of the crystal lattice. FIG. 8F shows a top view of functional photonic crystal microcavities oriented along the −60 degrees orientation of the crystal lattice. It is shown that geometry tuning can shift resonant frequencies and optimum spacing between microcavities ensures no cross-talk between adjacent microcavities.

Figure 1A:
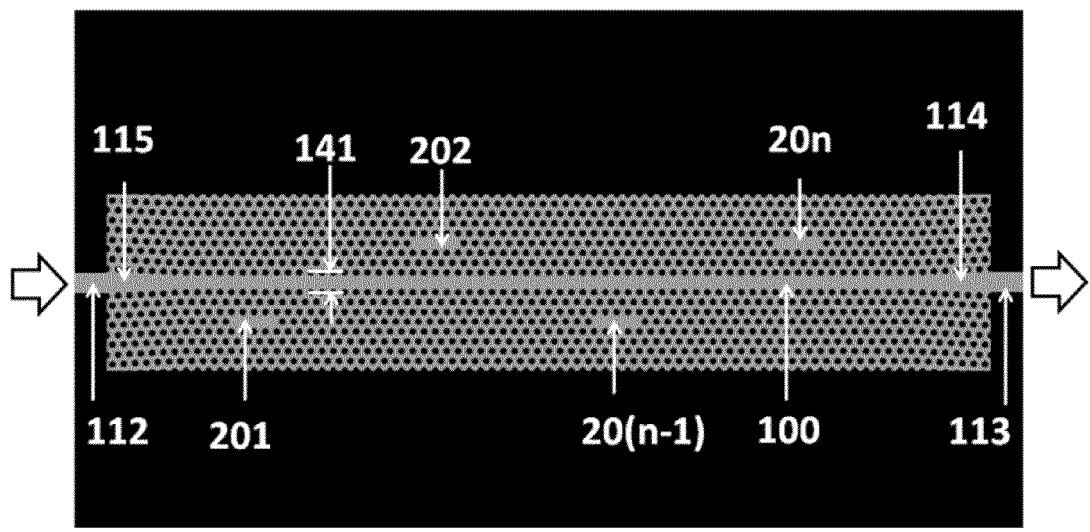
Figure 1B:
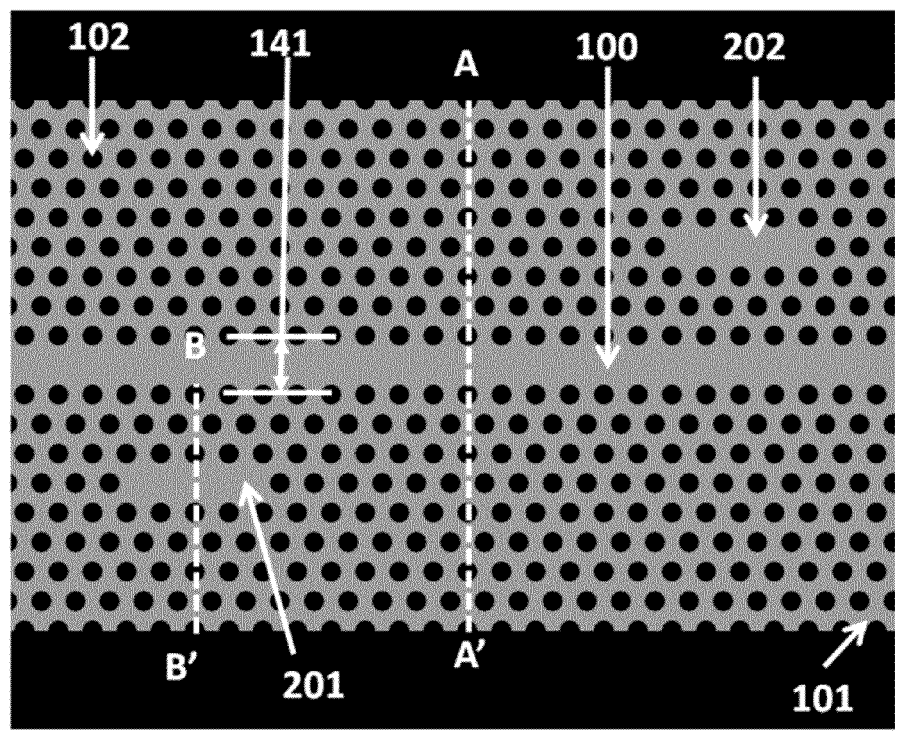
Figure 9:
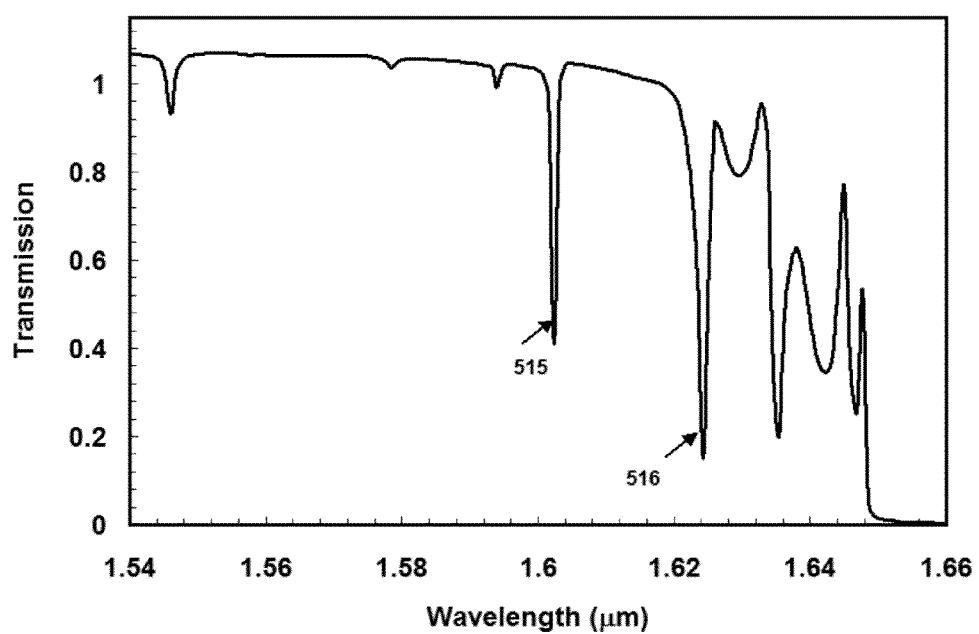

FIG. 9 shows another transmission spectrum of a functional photonic crystal waveguide with two representatively coupled photonic crystal microcavities of the embodiment depicted in FIG. 8A along the length of the functional photonic crystal waveguide in FIG. 1A and FIG. 1B. Two (2) microcavities are chosen, as a representative number for n. n can vary from 1 to N (N→∞). It is shown that geometry tuning can shift resonant frequencies and thereby allows the potential to couple N photonic crystal microcavities in an array, each with a small difference in geometry, hence a small difference in resonant frequency and hence potential of the device to respond to multiple analytes, molecules and biomolecules.

FIG. 10A through FIG. 10I show the steps in the fabrication of microfluidic channels on patterned silicon chips for biomolecule delivery and subsequent removal to create arrays of biomolecule coated photonic crystal microcavities.

Figure 10A:
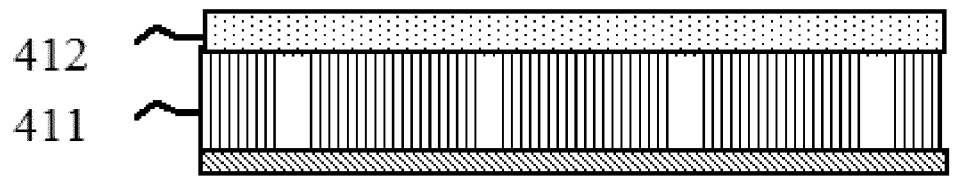
Figure 10B:
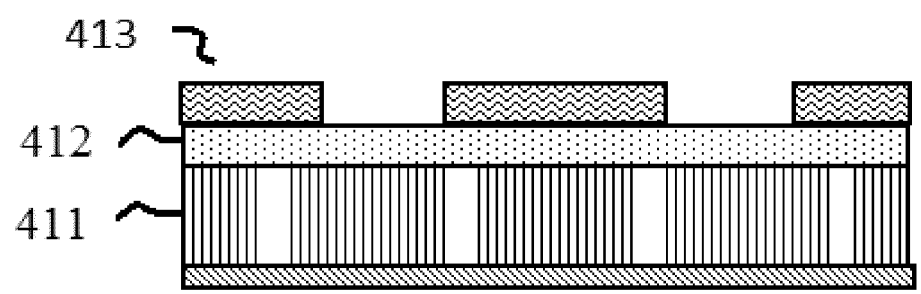
Figure 10C:
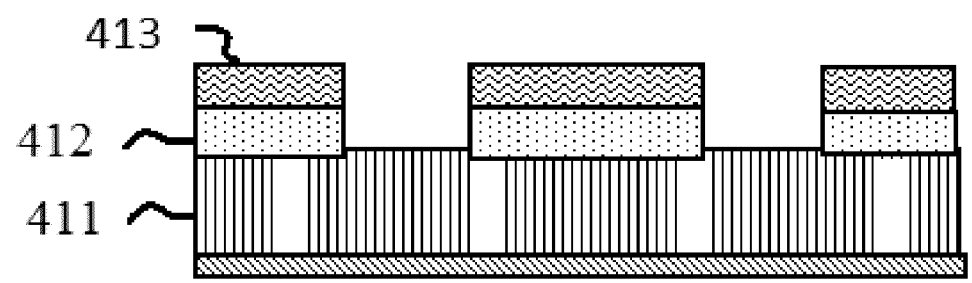
Figure 10D:
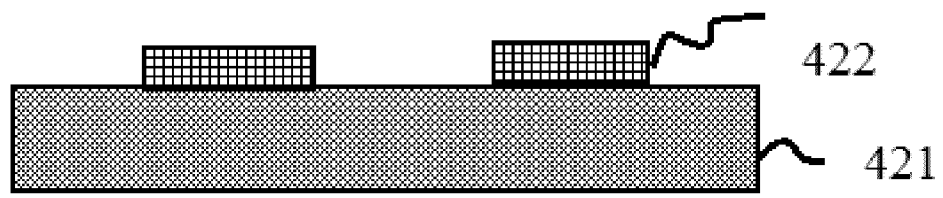
Figure 10E:
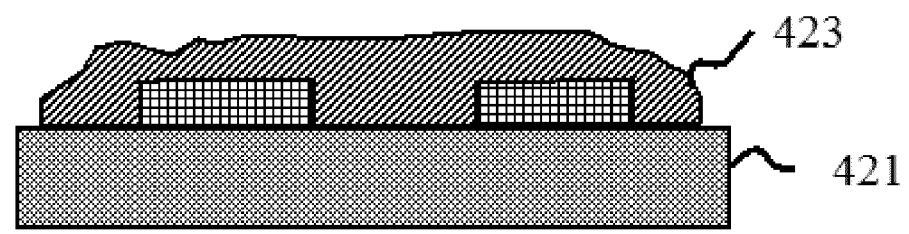
Figure 10F:
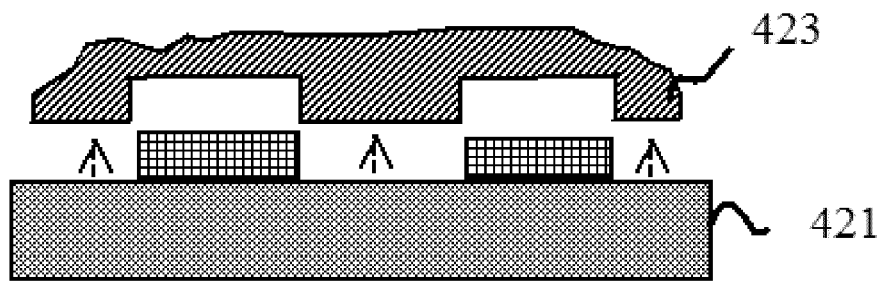
Figure 10G:
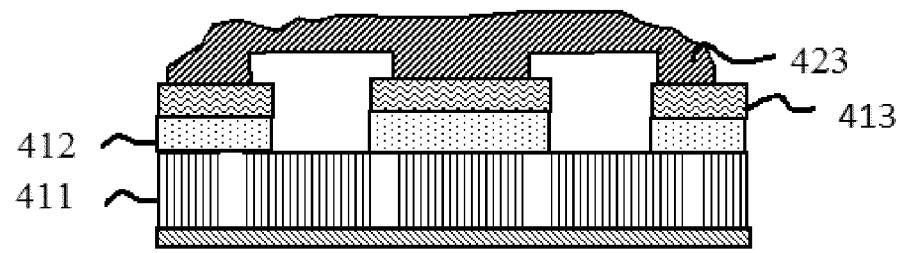
Figure 10H:
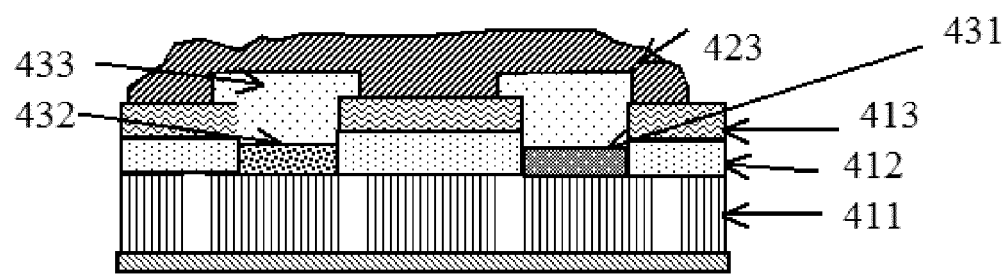
Figure 10I:
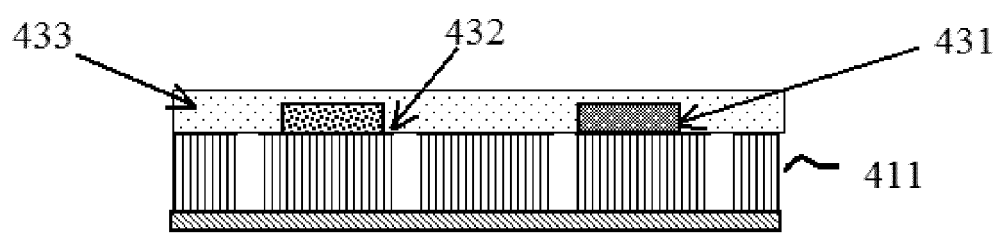
Figure 11:
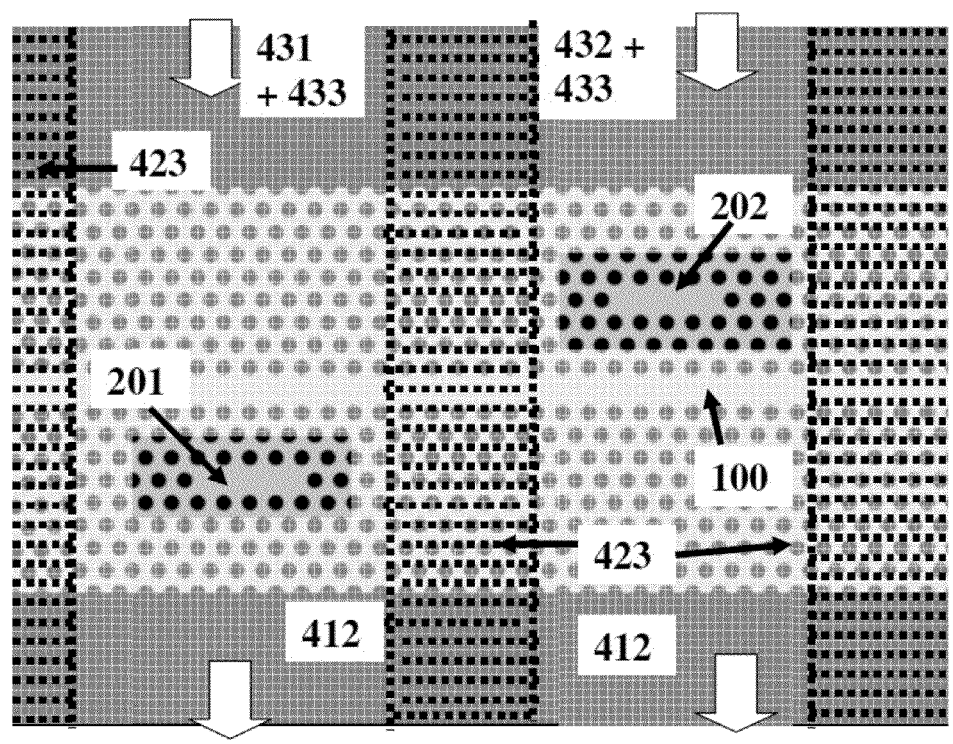

FIG. 11 is a top view of the device in FIG. 10G and FIG. 10H.

Figure 12A:
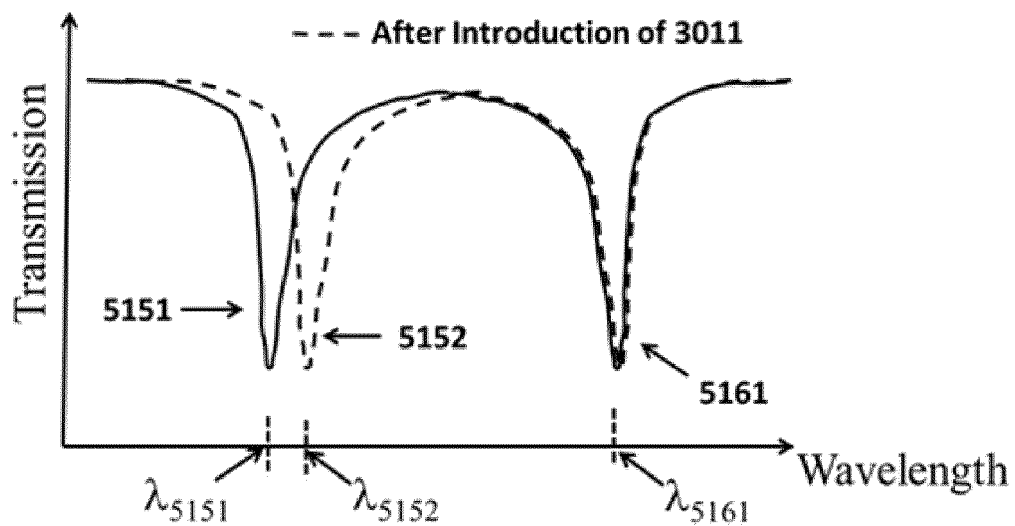
Figure 12B:
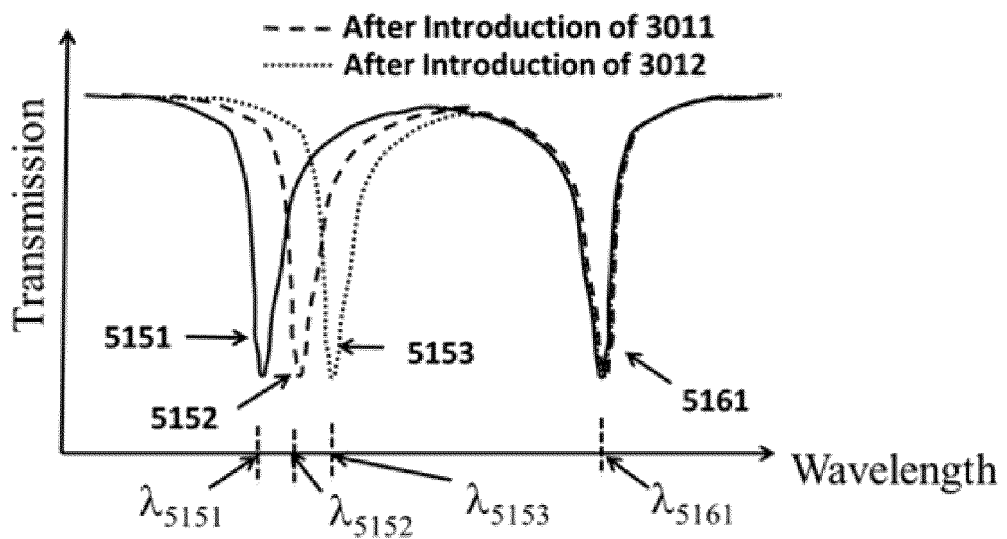

FIG. 12A and FIG. 12B show the changes in the transmission spectrum when a sandwiched measurement is performed that involves introduction of a secondary molecule or biomolecule after the introduction of the analyte molecule or biomolecule, resulting in amplification of the sensitivity detection and enhancement of the specificity detection.

V. DETAILED DESCRIPTION

Detailed Description of the Invention

In accordance with a preferred embodiment of the present invention, a device for a microarray for personalized diagnostic applications comprises: a functional photonic crystal waveguide having a waveguide core along which light is guided, arrays of photonic crystal microcavities along the length of the photonic crystal waveguide each coated with a separate biomolecule specific to disease identification, an input and output photonic crystal waveguide with gradually changed group index before and after the functional photonic crystal waveguide, which can bridge the refractive indices difference between conventional optical waveguides and the functional photonic crystal waveguide. The sensor can be used to detect organic or inorganic substances such as proteins, DNA, RNA, small molecules, nucleic acids, virus, bacteria, cells, and genes, without requiring labels such as fluorescence or radiometry. Light (from a broadband source or LED) coupled into a photonic crystal waveguide couples with the resonance of a photonic crystal microcavity and thereby drops the resonant wavelength in the microcavity, leading to a minimum in the transmission spectrum of the photonic crystal waveguide at the resonant wavelength. Transmission minima are observed for each resonant wavelength of the individual microcavities along the photonic crystal waveguide. The resonance wavelength shifts to longer wavelengths in response to the attachment of a material on the microcavity surface leading to the corresponding shift of the transmission minimum of that microcavity.

In another embodiment of the present invention, a device for a microarray for multiple analyte sensing applications comprises: a functional photonic crystal waveguide having a waveguide core along which light is guided, arrays of photonic crystal microcavities along the length of the photonic crystal waveguide each coated with a separate polymer or hydrogel specific to a unique environmental parameter, an input and output photonic crystal waveguide with gradually changed group index before and after the functional photonic crystal waveguide, which can bridge the refractive indices difference between conventional optical waveguides and the functional photonic crystal waveguide. The sensor can be used to detect changes in temperature, pressure, humidity, molarity of solution, acidity or alkalinity (pH) of aqueous medium, ion concentration of solutions, trace gases in the atmosphere, pollutants in ground water that can be organic or inorganic, volatile and non-volatile, pesticides and thereof in a single optical transmission measurement. A unique polymer or hydrogel is chosen with maximum response to changes in each of the above parameters and a unique microcavity along the waveguide is coated with a unique polymer or hydrogel. Light (from a broadband source or LED) coupled into a photonic crystal waveguide couples with the resonance of a photonic crystal microcavity and thereby drops the resonant wavelength in the microcavity, leading to a minimum in the transmission spectrum of the photonic crystal waveguide at the resonant wavelength. Transmission minima are observed for each resonant wavelength of the individual microcavities along the photonic crystal waveguide, in the pristine condition. The resonance wavelength shifts to longer wavelengths in response to changes in ambient parameters listed above leading to the corresponding shift of the transmission minimum of that microcavity, the amount of transmission minimum shift determines the absolute change in ambient conditions in the vicinity of the microarray device.

For the measurement of environmental parameters in situ, the device is incorporated with a filter to remove macroscopic dirt and dust particles. The filter can be a macroscopic filter incorporated off-chip or a microfluidic filter incorporated on-chip.

Methods for fabricating photonic crystal structures are widely described in the literature. Sensor structures of the invention have higher sensitivity than previous structures due to the use of two-dimensional photonic crystal microcavities with resonances that have high quality factor together with the slow light effect of two-dimensional photonic crystal waveguides. Methods for patterning of multiple biomolecules exclusively on photonic crystal microcavities that preserves biomolecule functionality in aqueous phase are disclosed. The amount of refractive index change and hence the shift in resonance frequency is determined by the amount of adsorbed molecules or biomolecules on the microcavity surface that interacts with the electromagnetic field of the photonic crystal. The system is capable of detecting a single cell attached to its surface.

Microarrays provide an unprecedented opportunity for comprehensive concurrent analysis of thousands of biomolecules such as proteins, genes, DNA molecules, small molecules or nucleic acids. The global analysis of the response to a toxic agent, as opposed to the historical method of examining a few select biomolecules, provides a more complete picture of toxicologically significant events. Array-based expression profiling is useful for differentiating compounds that interact directly with the species from those compounds that are toxic via a secondary mechanism. Microarrays are consequently finding numerous applications in pathogen detection and biodefense. The sensors have utility in the fields of pharmaceutical research (e.g., high throughput screening, secondary screening, quality control, cytoxicity, clinical trial evaluation), life science research (e.g., proteomics, protein interaction analysis, DNA-protein interaction analysis, enzyme-substrate interaction analysis, cell-protein interaction analysis), diagnostic tests (e.g., protein presence, cell identification), environmental detection (bacterial and spore detection and identification), and bio-warfare defense.

The principles of the invention can also be applied to e.g., evanescent wave based biosensors and any biosensors incorporating an optical waveguide. The principle can also be applied to arrays of ring or disk resonators coupled to a bus waveguide. However such waveguides provide limited freespectral range for microcavity resonances and also do not incorporate slow light effect of photonic crystal waveguides and are thus less sensitive with low signal-to-noise ratio.

Detailed descriptions of the preferred embodiments are provided herein. It is to be understood, however, that the present invention may be embodied in various forms. Therefore, specific details disclosed herein are not to be interpreted as limiting, but rather as a basis for the claims and as representative basis for teaching one skilled in the art to employ the present invention in virtually any appropriately detailed system, structure or manner.

Defect engineered photonic crystals, with sub-micron dimensions have already demonstrated high sensitivity to trace volumes of analytes. While biosensing has been demonstrated in photonic crystal devices with single biomolecules, no previous effort has been made to extend the device capability to microarrays. Particularly, patterning of multiple biomolecules on a few micron scales has faced challenges of binding exclusivity and binding specificity. Our proposed device consists of an array of photonic crystal microcavity resonators coupled to a single photonic crystal waveguide that give rise to minima in the photonic crystal waveguide transmission spectrum at the resonance frequency of the microcavity. Using a new microfluidic technique, individual target biomolecules are coated exclusively on individual photonic crystal microcavities. Our method eliminates labeling for analyte identification. The impact of our novel and robust multi-analyte sensing technique can reach much further than the field of biomolecular science and diagnostics alone. This section will provide detailed description of the preferred embodiments in the aspect of device architecture, as well as the design concept and working principle.

Figure 2:
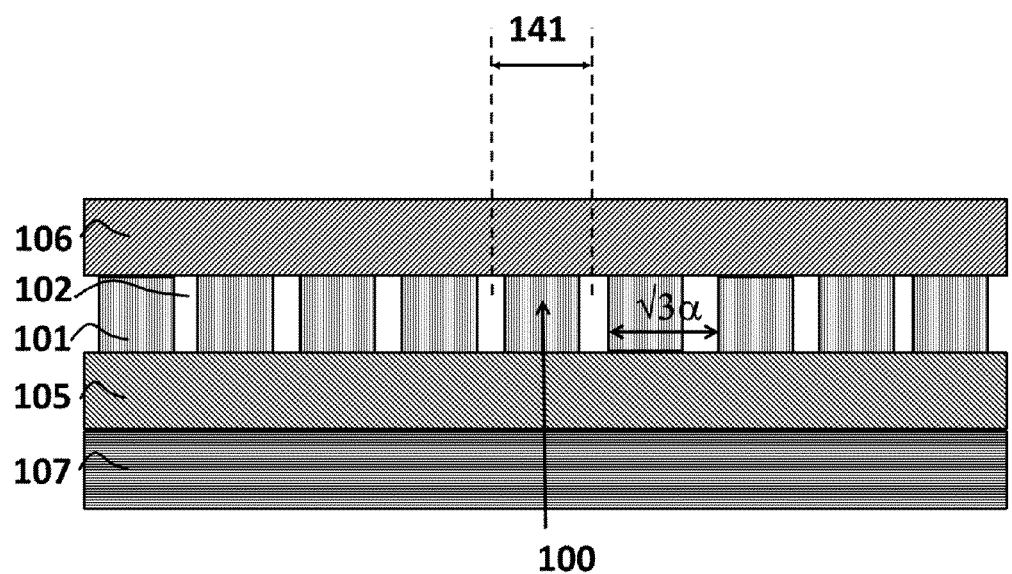
FIG. 2 is a cross-sectional view of the device shown in FIG. 1B taken along line A-A'.

FIG. 1A presents a schematic drawing of a photonic crystal microarray. It consists of a functional photonic crystal waveguide 100, input ridge waveguide 112, output ridge waveguide 113 and an array of N photonic crystal microcavities 20$n$ where n represents digits and ranges from 1 to N (N→∞). The functional photonic crystal waveguide 100 includes a number of column members 102 (labeled in FIG. 1B) etched through or partially into the semiconductor slab 101 (labeled in FIG. 1B). The waveguide core 141 is defined as the space between the centers of two column members adjacent to the region where the columns are absent. In one preferred embodiment, the column members 102 (labeled in FIG. 1B) are arranged to form a periodic lattice with a lattice constant α. In some embodiments, the width of waveguide core 141 can range from 0.5 times sqrt(3) times the lattice constant α to 50 times sqrt(3) times the lattice constant α. The arrows indicate the direction in which electromagnetic waves are coupled into and out of the photonic crystal waveguide respectively. In the figure, due to space limitations, the microcavities are designated as 201, 202, ..., 20($n$−1) and 20$n$ respectively. The photonic crystal microcavities are parallel to the photonic crystal waveguide and are placed 3 lattice periods away from the waveguide. Although the photonic crystal microcavities have been shown at 3 lattice periods away from the photonic crystal waveguide, the offset can be 1, 2, ... 10 lattice periods. Beyond 10 lattice periods, the coupling efficiency of light from the guided light in the photonic crystal waveguide will be very small. FIG. 1B is an enlarged section of FIG. 1A showing the photonic crystal microcavity elements 201, 202, columnar members 102, and photonic crystal waveguide 100 in greater detail. The photonic crystal waveguide 100 is defined by filling a complete row of columnar members with the semiconductor slab material 101. Similarly, a photonic crystal microcavity, for instance 201, is defined by filing a row of 4 columnar members 102 with semiconductor material 101. The distance between individual photonic crystal microcavities is 12 periods. The photonic crystal microcavity 201 can have different geometries as described in the literature. The resonant wavelength of a photonic crystal microcavity is dependent on the geometry of the microcavity. Light propagating in a photonic crystal waveguide couples to a photonic crystal microcavity at the resonant wavelength of the microcavity. The transmission spectrum of the photonic crystal waveguides consequently shows minima corresponding to the resonant wavelength of each photonic crystal microcavity. With reference to FIG. 2, which is a cross-sectional view of the functional photonic crystal waveguide 100 in FIG. 1B taken along line A-A', the column members 102 extend throughout the thickness of the slab 101 to reach a bottom cladding 105. In one embodiment, the top cladding 106 is air. However, the top cladding can be any organic or inorganic dielectric material, columnar members 102 can extend through both 106 and 101 as well as through the bottom cladding 105 to reach the substrate 107. Although the structure within the slab 101 is substantially uniform in the vertical direction in this embodiment, vertically non-uniform structure, such as the columnar members 102 whose radii are varying along the vertical direction, may be used as well. The column members 102 can be either simply void or filled with other dielectric materials. Between the ridge waveguide 112 and the core photonic crystal waveguide 100, there is an impedance taper 115 for coupling of light from ridge waveguide to photonic crystal waveguide with high efficiency. Similarly, at the output, between the photonic crystal waveguide 100 and the output ridge waveguide 113, there is another impedance taper 114 for better coupling efficiency. The impedance taper 115 is formed by shifting the columnar members from photonic crystal waveguide 100 to ridge waveguide 112 by x times α in the direction perpendicular to 100, in the plane of the waveguide, in steps of (x times α)/p where p is a number greater than 5, α is the lattice constant, and x varies from 0 to z, where z is a fractional number between zero and one (0<z<1). In FIG. 1A, p equals 8 since it is the first eight columnar members that have been shifted in both of the impedance tapers 115 and 114. In some embodiments, the impedance tapers 115 and 114 may be oppositely tapered. In that embodiment, impedance taper 115 would be narrower at the ridge waveguide 112 than at the photonic crystal waveguide 100 and impedance taper 114 would be narrower at the ridge waveguide 113 than at the photonic crystal waveguide 100. In this embodiment, x varies from 0 to z, where z is a fractional number between zero and minus one (−1<z<0). For a photonic crystal waveguide 100, 114 and 115, which comprise photonic crystals of two-dimensional periodicity, the wave guiding in the vertical direction must be provided by conventional index-guiding scheme. This means a bottom cladding 105 and a superstrate 106 with a lower effective index relative to that of the slab material must be disposed below and above the slab 101. In FIG. 2, the superstrate is absent and simply represented by air or vacuum. On one side, the bottom cladding 105 and superstrate 106 prevent guided lightwave escaping far away from the top and bottom surfaces of the slab 101. In most applications, it is desirable that the waveguide have a single guided mode, which can be achieved through adjusting the width of the waveguide core 141.

Figure 3:
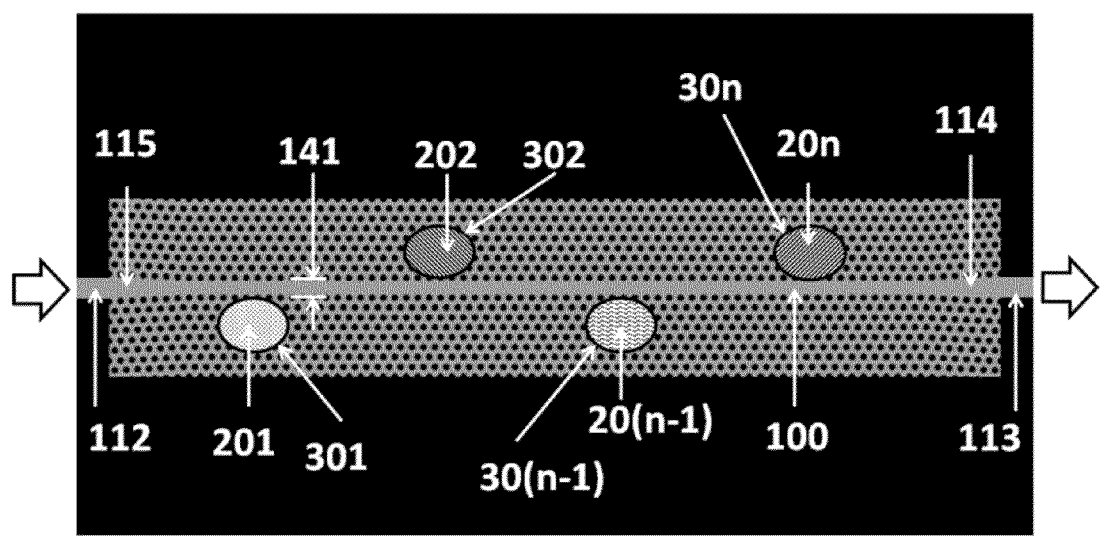
FIG. 3 is a top view of one embodiment of a photonic crystal microarray device based on an array of N photonic crystal microcavities coupled to a photonic crystal waveguide where each photonic crystal microcavity is coated with a different biomolecule.

In FIG. 3, substances are coated on the photonic crystal microcavity are labeled as 301, 302, ... 30($n$−1), 30$n$, where n represents digits and ranges from 1 to N (N→∞). Each photonic crystal microcavity 20$n$ is coated with a specific substance 30$n$. In one embodiment, the substance can be a biomolecule such as proteins, nucleic acids, DNA, RNA, antigens, antibodies, small molecules, peptides, genes etc. Each biomolecule can be specific to a particular disease causing conjugate where the disease of interest can be cancer, malaria, Leptospirosis or any infectious disease to achieve specific detection. In another embodiment, the substance 30*n* can be a hydrogel that swells in the presence of a specific analytical solution or ambient gas wherein the ambient gas includes, but is not limited to, greenhouse gases such as carbon dioxide, methane, nitrous oxide or other gases such as oxygen, nitrogen thereof. In yet another embodiment, the substance can be a polymer that changes its effective refractive index upon contact with a chemical substance or proportionately to changes in temperature, humidity and pressure thereof. The device is therefore a very generalized construction where multiple polymer or biological molecules, each specific to detection of a specific species, are arrayed for simultaneous detection.

Figure 4:
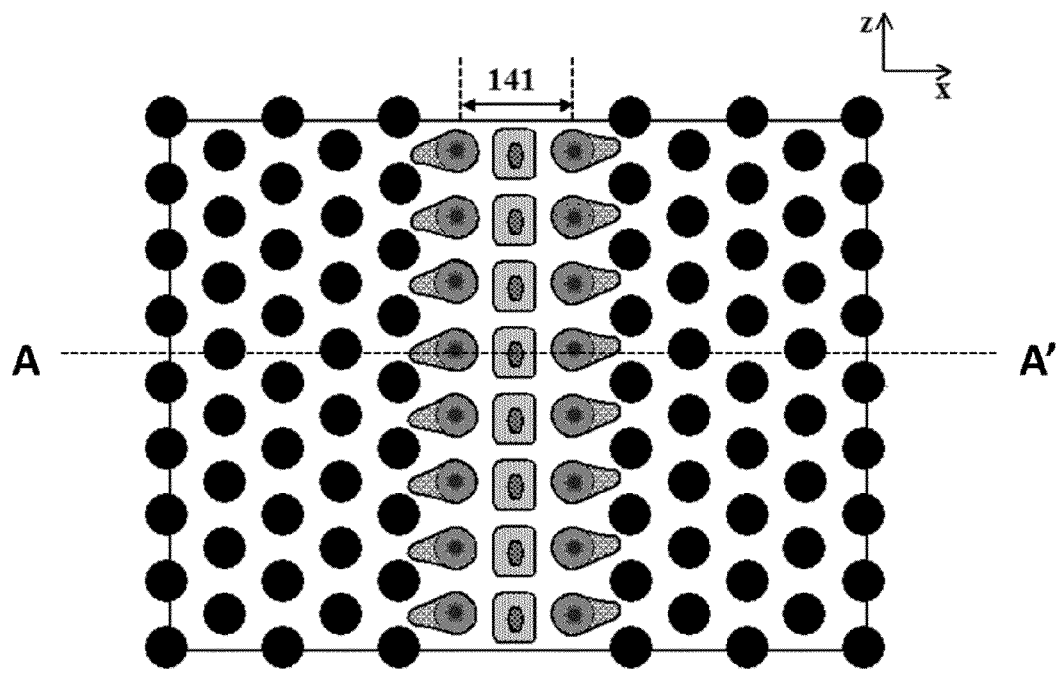
FIG. 4 is a top view of the field intensity pattern of a guided mode of a photonic crystal waveguide depicted in FIG. 1B taken along line A-A'.

FIG. 4 depicts a top view of the field intensity pattern of a guided mode of a waveguide 100 in FIG. 1 and FIG. 3. The circles indicate columnar members of the photonic crystal waveguide. It is seen in FIG. 4 that peak of the field intensity is well confined inside the waveguide core region 141. Outside of 141, there are two side peaks due to evanescent field. Due to even symmetry of the mode with respect to the center of the waveguide, the mode couples very well with resonant modes of photonic crystal microcavities which possess even symmetry.

Figure 5:
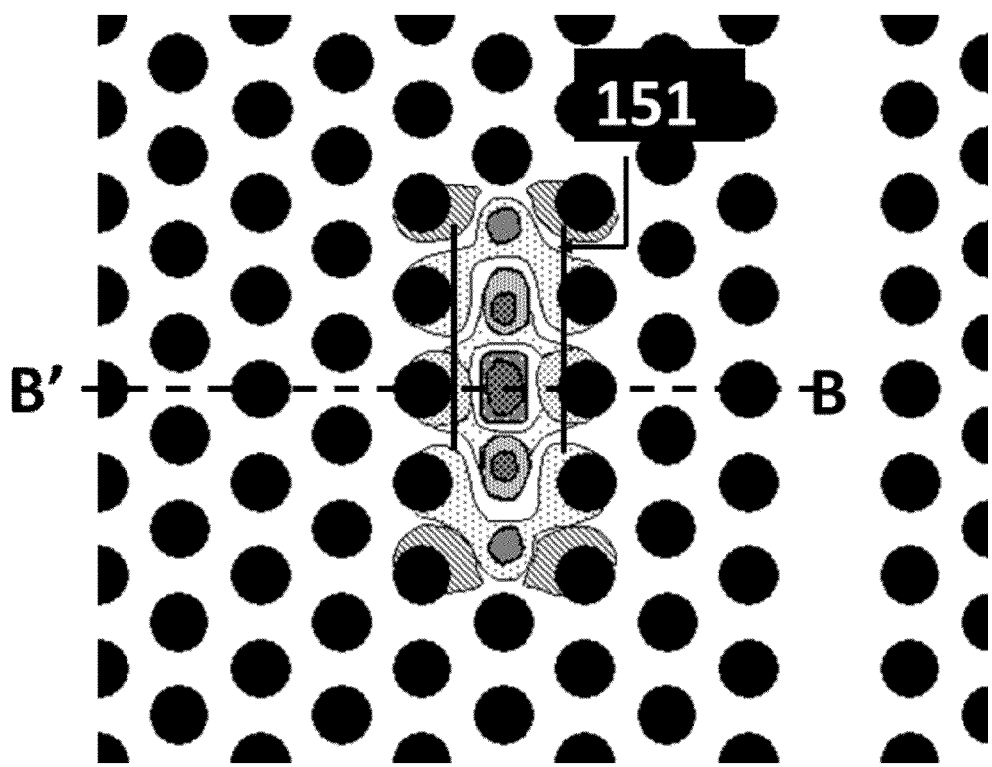
FIG. 5 is a top view of the field intensity pattern of a photonic crystal microcavity defect mode for the linear microcavity depicted in FIG. 1B taken along line B-B'.

FIG. 5 depicts a top view of the field intensity pattern of a defect mode of a photonic crystal microcavity 20*n* where n represents digits and ranges from 1 to N (N→∞), in FIG. 1 and FIG. 2. The circles indicate columnar members of the photonic crystal microcavity. It is seen in FIG. 5 that peak of the field intensity is well confined inside the photonic crystal microcavity region 151. Outside of 151, there is very weak field intensity that overlaps with the columnar members. FIG. 5 suggests that photonic crystal microcavity resonant mode is well confined in the dielectric, in the plane of the waveguide inside region 151.

Figure 6:
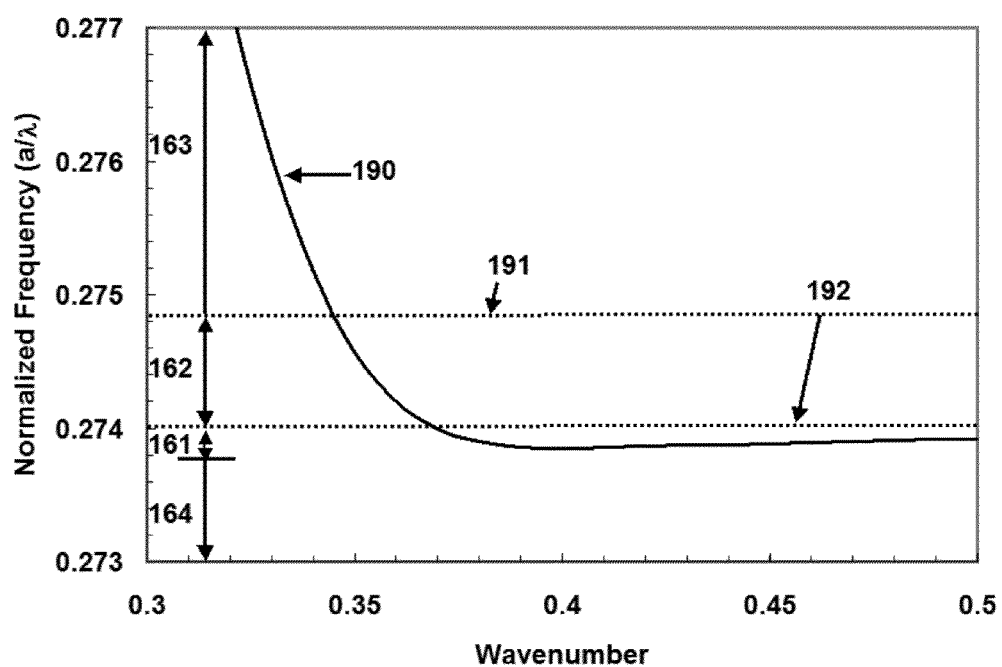
FIG. 6 illustrates a typical diagram of the dispersion relation of a photonic crystal waveguide and individual microcavities with resonant modes in the low dispersion low group velocity region for enhanced mode coupling from waveguide to microcavity.

The bold curve 190 in FIG. 6 depicts a dispersion diagram of the photonic crystal waveguide 100. Three regions are distinctly visible in the bold curve. A region 161 where $d\omega/dk$ is almost zero, a region 163 where $d\omega/dk$ is very high and a region 162 where $d\omega/dk$ has intermediate values. $d\omega/dk$ denotes the group velocity of light propagating in the photonic crystal waveguide at the corresponding frequency. The region 164 denotes the stopgap of the photonic crystal waveguide where the transmission is zero. The coupling efficiency between a photonic crystal waveguide and a photonic crystal microcavity is inversely proportional to the group velocity, consequently slower the group velocities higher the coupling due to higher interaction time. However, region 161 is not suitable due to high dispersion and consequently high transmission loss. We identify a range of frequencies in region 162 between dotted lines 191 and 192 over which we vary the resonance of the photonic crystal microcavity to achieve high coupling efficiency with photonic crystal waveguide 100.

FIG. 7, FIG. 8, FIG. 9 address photonic crystal microcavity design issues so that the entire range of frequencies between the dotted lines 191 and 192 can be efficiently used for resonant coupling, thereby increasing the number of microcavities that can be arrayed in parallel for the multiple analyte sensing diagnostic chip. FIG. 7A depicts one embodiment of a photonic crystal microcavity where a row of 4 columnar members 102 has been filled with the semiconductor dielectric material 101. We consider a photonic crystal waveguide transmission spectrum when 2 photonic crystal microcavities say 201 and 202 in FIG. 1 are coupled to the photonic crystal waveguide 100. For the microcavity 201, the columnar members 501 and 502, have each been shifted toward each other by 0.2α and for microcavity 202 the columnar members 503 and 504 have each been shifted away from each other by 0.2α, where a denotes the lattice periodicity of the triangular lattice photonic crystal structure. In FIG. 7B, 2 sharp minima 511 and 512 are observed that correspond to the resonance of corresponding photonic crystal microcavities 201 and 202. This demonstrates that progressive geometry tuning of photonic crystal microcavities can result in multiple microcavities arrayed along a photonic crystal waveguide, each with a unique resonance frequency resulting in a unique transmission minimum in the photonic crystal waveguide 100 transmission spectrum. Although the magnitude of the shift is indicated as 0.2α, the magnitude of the shift can vary continuously from 0 to 0.45α.

FIG. 8A depicts another embodiment of a photonic crystal microcavity where a row of 4 columnar members 102 has been filled with the semiconductor dielectric material 101. We consider a photonic crystal waveguide transmission spectrum when 2 photonic crystal microcavities say 201 and 202 in FIG. 7A are coupled to the photonic crystal waveguide 100. The individual construction of each of the photonic crystal microcavities 201 and 202 in FIG. 7A can be described by the microcavity in FIG. 8A. As in FIG. 7A, for the microcavity 201, the columnar members 501 and 502, have each been shifted toward each other by 0.2α and for microcavity 202 the columnar members 503 and 504 have each been shifted away from each other by 0.2α, where a denotes the lattice periodicity of the triangular lattice photonic crystal structure. For the microcavity 202, as illustrated in general for a microcavity 20*n*, the diameters of the members 601-610 are further reduced in size to 0.9 times the diameter of columnar members 102 elsewhere. Two sharp minima 513 and 514 are observed that correspond respectively to the resonance of corresponding photonic crystal microcavities 201 and 202. The transmission minimum 514 is red-shifted corresponding to the transmission minimum 512 in FIG. 7B. The transmission minimum 513 is not shifted corresponding to the transmission minimum 511 in FIG. 7B since the geometry of microcavity 201 has not been changed from FIG. 7A. The fact is significant since this ensures that our design selection of 12 lattice periods between adjacent microcavities is optimum and does not alter either a resonance quality factor or the resonance wavelength of a designed microcavity. By reducing the diameter of the columnar members 601-610, the dielectric fraction inside the resonant mode of 202 is increased which brings the frequency of the mode down, closer to the dotted line 192 in FIG. 6. The diameter of the columnar members 601-610 can thus be changed in step to achieve a new microcavity design with a different resonant frequency. Although the magnitude of the shift for elements 501 and 502 is indicated as 0.2α, the magnitude of the shift can vary continuously from 0 to 0.45α. Although the magnitude of the diameter change of the members 601-610 is indicated as 0.9 times the diameter of columnar members 102 elsewhere, the magnitude of the shift can vary continuously from 0 to 1 times the diameter of columnar members 102 elsewhere.

Referring to FIG. 8, columnar members 501 and 502 are not the only columnar members that may be shifted. Surrounding columnar members such as 601-610 may also be shifted towards the interior or exterior of the microcavity 20*n*. In one embodiment, columnar member 501 may be shifted by 0.2α in the Γ–K direction arrow shown in FIG. 8A, columnar member 502 may be shifted by 0.2α in the direction opposite to the Γ–K direction arrow shown in FIG. 8A, all columnar members 601-610 may be shifted by 0.2α, in the direction arrows for each element 601-610 shown in FIG. 8A. In another embodiment, columnar member 501 may be shifted by 0.2α opposite to the Γ–K direction arrow shown in FIG. 8A, columnar member 502 may be shifted by 0.2α in the direction of the Γ–K direction arrow shown in FIG. 8A, all columnar members 601-610 may be shifted by 0.2α, in the direction opposite to the arrows for each element 601-610 shown in FIG. 8A. Although the magnitude of the shift is indicated as 0.2α, the magnitude of the shift can vary continuously from 0 to 0.45α. Additionally, the columnar members 601-610 may also be shifted at any angle from 0 to 360 degrees relative to the Γ–K direction arrow in FIG. 8A. Similarly, columnar members 501 and 502 may be shifted by 0.2α, at any angle from 0 to 360 degrees relative to the Γ–K direction arrow in FIG. 8A.

FIG. 9 depicts another embodiment of a photonic crystal microcavity where a row of 4 columnar members 102 has been filled with the semiconductor dielectric material 101. We consider a photonic crystal waveguide transmission spectrum when 2 photonic crystal microcavities say 201 and 202 in FIG. 7A are coupled to the photonic crystal waveguide 100. For the microcavity 201, the columnar members 501 and 502, have been shifted by −0.2α and for microcavity 202 the columnar members 503 and 504 are shifted by +0.2α, where a denotes the lattice periodicity of the triangular lattice photonic crystal structure. For the microcavity 202, the diameters of the members 601-610 are reduced in size to 0.9 times the diameter of columnar members 102 elsewhere. For the microcavity 201, the diameters of the members 601-610 are increased in size to 1.05 times the diameter of columnar members 102 elsewhere. Two sharp minima 515 and 516 are observed that correspond respectively to the resonance of corresponding photonic crystal microcavities 201 and 202. The transmission minimum 515 is blue-shifted corresponding to the transmission minimum 511 in FIG. 7B. The transmission minimum 516 is red-shifted corresponding to the transmission minimum 514 in FIG. 8B and red-shifted further corresponding to the transmission minimum 512 in FIG. 7B. By further reducing the diameter of the columnar members 601-610 compared to FIG. 8B, the dielectric fraction inside the resonant mode of 202 is further increased which brings the frequency of the mode down further, and even closer to the dotted line 192 in FIG. 6. By increasing the diameter of the columnar members 601-610, the dielectric fraction inside the resonant mode of 201 is decreased, which raises the frequency of the resonant mode, closer to the dotted line 191 in FIG. 6. The diameter of the columnar members 601-610 can thus be changed in steps to achieve a new microcavity design with a different resonant frequency. Although the magnitude of the diameter change of the members 601-610 is indicated as 1.05 times the diameter of columnar members 102 elsewhere, the magnitude of the shift can vary continuously from 1 to 2 times the diameter of columnar members 102 elsewhere. In yet another embodiment, the columnar members 501, 502 and 601-610 in FIG. 8A can be selectively filled with a material with the same or different dielectric constant as the dielectric constant of the slab material to achieve a different resonance frequency of the photonic crystal microcavity.

In another embodiment shown in FIG. 8C, the columnar members 501, 501a, and 501b and 502, 502a, and 502b of microcavity 20n may be changed in diameter and/or shifted in position to achieve a desired resonance frequency of the photonic crystal microcavity. By making these and other similar geometry changes to the columnar members surrounding the microcavity as shown for FIG. 7A and FIG. 8A and described for FIG. 9 above, for each of the microcavities 201, 202, . . . 20n in FIG. 1, it is possible to shift the transmission minima of the individual microcavities so that they do not overlap. The idea is to have as many first order transmission minima from the varied microcavities without interference from the second order transmission minima. One such second order transmission minima from the same microcavity as transmission minimum 512 can be seen in FIG. 7B just to the left of transmission minimum 511 at around 1580 nm.

In another embodiment shown in FIG. 8D, each microcavity 201, 202, . . . 20n in FIG. 1A and FIG. 1B may be mirrored or duplicated on the opposite side of the photonic crystal waveguide. The microcavity 201 and the mirror microcavity 201a would have the same spacing between void columnar members adjacent to the microcavity 201 and microcavity 201a and the same diameter of void columnar members adjacent to the microcavity 201 and microcavity 201a. The composite microcavity, comprising microcavities 201 and 201a thus has a larger optical mode volume resulting in higher sensitivity to refractive index changes. In other embodiments, microcavities oriented along the crystal lattice of +60 degrees and −60 degrees as shown in FIG. 8E and FIG. 8F, respectively, may also be mirrored or duplicated directly across the photonic crystal waveguide.

In another embodiment shown in FIG. 8E and FIG. 8F, the microcavities are oriented along another orientation of the crystal lattice. Although the photonic crystal microcavities 201, 202, . . . 20n in FIG. 1 have been shown parallel to the photonic crystal waveguide, parallel to the direction of propagation of light in the core, the array can be oriented next to the photonic crystal waveguide along any of the lattice directions at +60 degrees or −60 degrees to the photonic crystal waveguide as shown in FIG. 8E and FIG. 8F, respectively. All descriptions as shown for FIG. 7A and FIG. 8A and described for FIG. 9 would be applied similarly with respect to the orientations shown by FIG. 8E and FIG. 8F. Although the photonic crystal microcavities in FIG. 8E and FIG. 8F have been shown drawn at 3 periods away from the photonic crystal waveguide along the respective orientations, the offset can be 1, 2, . . . 10 lattice periods. Beyond 10 lattice periods, the coupling efficiency of light from the guided light in the photonic crystal waveguide will be very small.

The second design concept of this invention is depicted in FIG. 10 that concerns the patterning of biomolecules onto the patterned silicon substrate 411 using a novel microfluidic technique that preserves biomolecule functionality in aqueous phase at all times. In one embodiment, biomolecules are patterned on a photonic crystal patterned silicon substrate with a thin layer of silicon dioxide. The thickness of silicon dioxide is not more than 10 nanometers. FIG. 10 shows the steps in the fabrication process on a patterned substrate that preserves the biomolecule functionality in aqueous phase. A film, 412 is deposited on the substrate in FIG. 10A. In one embodiment, the film 412 is parylene. A thin film of metal 413 is sputtered onto the film 412 and patterned by photolithography. (FIG. 10B). In one embodiment, the film is aluminum but it could be any metal that can be sputtered onto the film 412. Using 413 mask, 412 is etched to substrate in oxygen plasma. (FIG. 10C). The film 412 is patterned so that only the region above the microcavity is opened. In one embodiment, when the device is to be used as a biosensor, the devices are functionalized by treating with 10% by volume 3-aminopropyl-triethoxy-silane (3-APTES) in toluene. It is then washed 3 times in toluene to remove unbound 3-APTES, 3 times in methanol to remove toluene and finally 3 times in de-ionized water to remove methanol. The devices are then incubated in 1% glutaraldehyde in phosphate buffered saline (PBS) for 5 minutes and washed 3 times in PBS. Simultaneously, PDMS microfluidic channels are prepared by molding technique. A master silicon wafer 421, cleaned in Piranha solution and rinsed is dried and subsequently, a photoresist 422 is spin-coated on the silicon wafer. In one embodiment, the photoresist is SU-8 but it can be any lithographically patterned polymer that can give high aspect ratio features. After patterning 422 (FIG. 10D) and baking, a mixture of another polymer precursor 423 and curing agent in the ratio of 10:1 volume together with a hydrophilic additive is poured over the 422 mold, as shown in FIG. 10E. In this embodiment the polymer 423 is polydimethylsiloxane, popularly known as PDMS. After complete curing, the 423 layer will be removed from the mold to achieve the structure as shown in FIG. 10F. The PDMS microfluidic channel is carefully aligned and mounted on the structure patterned in FIG. 10C, as shown in FIG. 10G. Solutions 433 containing different biomolecule samples 431, 432 will be introduced into microchannels as illustrated in FIG. 10H. Biomolecules will be selectively deposited on exposed sites in each channel on the photonic crystal microcavity. After initial biomolecule deposition and overnight incubation, microchannels will be thoroughly washed with PBS to purge them of any excess, unbound biomolecule and the microchannels peeled off using tweezers. After overnight incubation and washing, the device is coated with bovine serum albumin (BSA) to prevent any non-specific binding and washed 3 times with PBS. Finally, the device as a whole is maintained in solution 433 as shown in FIG. 10I. The final photonic crystal microcavities coupled to waveguide microarray device with patterned proteins has been shown schematically in FIG. 3.

In another embodiment, the individual biomolecules are dispensed on top of the individual photonic crystal microcavities by an ink jet printer. In this embodiment, devices are functionalized by treating with 10% by volume 3-APTES (APTES=amino-propyl-triethoxy silane) in toluene. It is then washed 3 times in toluene to remove unbound 3-APTES, 3 times in methanol to remove toluene and finally 3 times in de-ionized water to remove methanol. The devices are then incubated in 1% glutaraldehyde in phosphate buffered saline (PBS) for 5 minutes and washed 3 times in PBS. Target biomolecules in glycerol are ink-jet printed with precision on top of the photonic crystal microcavities. A unique biomolecule 301 is printed on individual photonic crystal microcavity 201. The printed spots were left to incubate overnight. Subsequently, all target antibodies not bound to the functionalized device layer were removed by washing 3 times in PBS. After overnight incubation and washing, the device is coated with bovine serum albumin (BSA) to prevent any non-specific binding and washed 3 times with PBS. No microfluidic channels are needed in this embodiment. The final photonic crystal microcavities coupled to waveguide microarray device with patterned proteins has been shown schematically in FIG. 3.

FIG. 11 is the top view of the device in FIG. 10G and FIG. 10H. As illustrated, openings in the parylene (412) are lithographically defined so that the photonic crystal microcavity regions of 201 and 202 are exposed. The procedure applies to all microcavities 20n. The PDMS microchannels are depicted by the dotted elements 423. Molecules and target biomolecules 431 and 432 corresponding respectively to biomolecular specific coatings on photonic crystal microcavities 201 and 202 are flown in through the microfluidic channels in the direction of the arrows. Biomolecules 431 and 432 correspond to 301 and 302 respectively in FIG. 3. Since the open areas in 412 have been silanized, biomolecules 301 (431) and 302 (432) preferentially bind to the photonic crystal substrate above the photonic crystal microcavities 201 and 202 respectively. The same principle applies to all N photonic crystal microcavities arrayed along the length of the photonic crystal waveguide 100. Thus, there is no cross-contamination between 301 (431) and 302 (432).

FIG. 12A and FIG. 12B show how the detection sensitivity can be amplified as well as how more confidence is derived regarding the selectivity or specificity of the binding between an analyte molecule or biomolecule and its corresponding molecule or biomolecule on the one or more optical microcavities. The detection sensitivity of the device is determined from the magnitude of the shift in the minimum in the transmission intensity corresponding to the magnitude of the change in the resonance frequency of the resonance mode of the corresponding photonic crystal microcavity. The specificity of the detection is determined by the binding of the analyte molecule or biomolecule only to specific polymer molecules or biomolecules. Sensitivity amplification is achieved by an enhancement of the magnitude of the shift by the secondary molecule or biomolecule. Enhancement of detection specificity is achieved by the binding of the analyte molecule or biomolecule to two polymer molecules or biomolecules, namely, the polymer molecule or biomolecule attached to the photonic crystal microcavity device, and the secondary polymer molecule or biomolecule introduced in solution. The principle is described with respect to the resonance 515 in FIG. 9. We consider that $\lambda_{5151}$ is the minimum in the transmission wavelength corresponding to the resonance 5151 of the particular photonic crystal microcavity 201 that is coated with a polymer molecule or biomolecule 301 as in FIG. 3. We consider that $\lambda_{5161}$ is the minimum in the transmission wavelength corresponding to the resonance 5161 of the particular photonic crystal microcavity 202 that is coated with a polymer molecule or biomolecule 302 as in FIG. 3. When an analyte molecule or biomolecule 3011 that binds to 301 is introduced in solution, a resonance wavelength shift is observed and the resonance minimum $\lambda_{5151}$ in the transmission spectrum shifts to the new wavelength position $\lambda_{5152}$ corresponding to the changed resonance 5152 of the photonic crystal microcavity 201 coated with polymer molecule or biomolecule 301. The net wavelength shift is thus ($\lambda_{5152}$ minus $\lambda_{5151}$) where $\lambda_{5152}$ is greater in magnitude than $\lambda_{5151}$. No resonance wavelength shift will be observed in the resonance $\lambda_{5161}$. When a secondary polymer molecule or biomolecule 3012 is next introduced in solution, which also binds to the analyte molecule or biomolecule 3011 that has bound to 301, a secondary resonance wavelength shift is observed and the transmission minimum $\lambda_{5152}$ shifts to a new transmission minimum $\lambda_{5153}$ corresponding to the further modified resonance frequency of the photonic crystal microcavity 201. The analyte molecule or biomolecule 3011 is thus sandwiched between the two polymer molecules or biomolecules 301 and 3012, both of which recognize the analyte molecule or biomolecule 3011. No resonance wavelength shift is observed in the transmission minimum at $\lambda_{5161}$ corresponding to the resonance 5161 that corresponds to the resonance frequency of the photonic crystal microcavity 202 that is coated with a polymer molecule or biomolecule 302 that does not bind to the analyte molecule or biomolecule 3012. The secondary wavelength shift due to the sandwich thus amplifies the resonance wavelength shift of the corresponding photonic crystal microcavity to ($\lambda_{5153}$ minus $\lambda_{5151}$) where ($\lambda_{5153}$ minus $\lambda_{5151}$) is greater than ($\lambda_{5152}$ minus $\lambda_{5151}$) and represents a method of amplifying the sensitivity in label-free optical microarrays. In addition, the secondary wavelength shift due to the sandwich further proves that the analyte molecule or biomolecule 3011 that has bound to 301 on top of the photonic crystal microcavity 201 is indeed the analyte molecule or biomolecule 3011 that must be detected and is not any other non-selective molecule or biomolecule which sticks to the molecule or biomolecule due to other physical reasons not determined by the binding kinetics between 301 and 3011. In addition to sensitivity amplification, the sandwiched detection method applied to the photonic crystal label free microcavity thus adds to detection specificity and detection selectivity. The sensor surface 201 may be regenerated by removing the analyte molecules or biomolecules 3011 and the secondary molecules or biomolecules 3012 by subjecting the sensor device to appropriate solutions such as solutions with a low pH. Consequently, in FIG. 12A and FIG. 12B, after regeneration, the resonance wavelength $\lambda_{5153}$ or $\lambda_{5152}$ returns to $\lambda_{5151}$.

Although the method in FIG. 12A and FIG. 12B above has been described with respect to photonic crystal microcavities 201 and 202, one skilled in the art will note that the method can be applied with respect to all photonic crystal microcavities 201, 202, . . . 20(n−1), 20n in FIG. 1A.

In one embodiment, the slab 101 is formed from a material of high refractive index including, but not limited to, silicon, germanium, carbon, gallium nitride, gallium arsenide, gallium phosphide, indium nitride, indium phosphide, indium arsenide, zinc oxide, zinc sulfide, silicon oxide, silicon nitride, alloys thereof, metals, and organic polymer composites. Single crystalline, polycrystalline, amorphous, and other forms of silicon may be used as appropriate. Organic materials with embedded inorganic particles, particularly metal particles, may be used to advantage. In one embodiment, the top cladding 106 and bottom cladding 105 are formed from a material whose refractive index is lower than that of the slab material. Suitable top cladding and bottom cladding materials include, but not limited to, air, silicon oxide, silicon nitride, alumina, organic polymers and alloys thereof. The substrate 107 materials include, but not limited to, silicon, gallium arsenide, indium phosphide, gallium nitride, sapphire, glass, polymer and alloys thereof. In one embodiment, the columnar members 102 are formed from a material whose refractive index is substantial different from that of the slab 101. Suitable materials for the columnar members 102 include, but not limited to, air, silicon oxide, silicon nitride, alumina, organic polymers, or alloys thereof. In one preferred embodiment, the slab 101 is formed from silicon, the columnar members 102 are formed from air, the top cladding 106 is air, and the bottom cladding 105 is formed from silicon oxide, while the substrate 107 is silicon.

Although the word "biomolecule" is used in the preceding discussions, one skilled in the art will understand that it refers to a general form of biomolecule that includes, but not limited to, proteins, deoxyribonucleic acid (DNA), ribonucleic acid (RNA), genes, antigens, antibodies, small molecules, nucleic acids, bacteria, viruses and any arrayed combination thereof for the specific diagnosis of diseases. "Molecule" can denote any polymer or hydrogel that responds to changes in the ambient medium of the device. Any combination of "molecules" and "biomolecules" can be arrayed on the device to get precise knowledge of process conditions, system conditions, analyte identification and/or binding events for disease identification.

Although the word "light" or "lightwave" is used to denote signals in the preceding discussions, one skilled in the art will understand that it refers to a general form of electromagnetic radiation that includes, and is not limited to, visible light, infrared light, ultra-violet light, radios waves, and microwaves.

In summary, the present invention provides an ultra compact microarray device architecture using two-dimensional photonic crystal microcavities coupled to a single photonic crystal waveguide, together with a new microfluidic technique that preserves the biomolecule functionality in aqueous phase. The invention enables massively parallel, label-free, on-chip multi-analyte sensing for biochemical sensing and a diagnostic assay for any disease, which displays target-probe biomolecule conjugation. The biomolecule of interest can be DNA, RNA, proteins, nucleic acids and small molecules. It incorporates a new microfluidic technique with photonic crystal devices, that allows patterning of biomolecules in the aqueous phase. Owing to the small dimensions of the devices presented herein, one can monolithically integrate the photonic crystal microarrays on silicon VLSI chips. The CMOS compatible photonic crystal microarray devices have simpler design requirements than the microelectronics industry. Furthermore, easy regeneration capability and high measurement throughput ensures that our miniature compact devices will deliver improved results with significantly lower cost to the customer. The device is of extreme significance in basic biological sciences and human health diagnostics, as well as in the food and beverage industry and in bio-warfare defense.

While the invention has been described in connection with a number of preferred embodiments, it is not intended to limit the scope of the invention to the particular form set forth, but on the contrary, it is intended to cover such alternatives, modifications, and equivalents as may be included within the design concept of the invention as defined by the appended claims.

The invention claimed is:

1. A label-free analyte detection apparatus comprising a photonic crystal waveguide and an array of photonic crystal microcavities and further comprising:
   i) a substrate;
   ii) a slab disposed on the substrate;
   iii) a plurality of void columnar members etched through the slab, wherein the plurality of void columnar members form a periodic lattice with a lattice constant $\alpha$;
   iv) a core in the slab having an input side and an output side;
   v) the photonic crystal waveguide formed within the core by a row of void columnar members from the input side to the output side, wherein the row of void columnar members is filled with the material of the slab;
   vi) an input impedance taper in the photonic crystal waveguide at the input side;
   vii) an input ridge waveguide in the core coupled to the input impedance taper in the photonic crystal waveguide, along the slab, wherein the input impedance taper is configured to couple the electromagnetic radiation between the input ridge waveguide and the core;
   viii) an output impedance taper in the photonic crystal waveguide at the output side; and
   ix) an output ridge waveguide in the core coupled to the output impedance taper in the photonic crystal waveguide, along the slab, wherein the output impedance taper is configured to couple the electromagnetic radiation between the core and the output ridge waveguide;
wherein the array of photonic crystal microcavities comprise one or more optical microcavities formed by a group of columnar members, wherein the group of columnar members is filled with the material of the slab and wherein the one or more optical microcavities are at an angle of 0 degrees, +60 degrees, or −60 degrees relative to the core and are separated from each other and the photonic crystal waveguide by one or more lattice constants;
wherein the photonic crystal waveguide supports one or more guided modes of a broadband source;

wherein each of the one or more optical microcavities are uniquely tuned to support one or more resonance modes;

wherein the one or more optical microcavities are tuned by changing at least one of: the spacing of the void columnar members adjacent to the one or more optical microcavities and the diameter of the void columnar members adjacent to the one or more optical microcavities;

wherein each of the one or more optical microcavities along the photonic crystal waveguide has a unique resonance frequency that does not overlap with the resonance frequency of any other optical microcavity along the photonic crystal waveguide;

wherein the array of photonic crystal microcavities with one or more target binding molecules coated on the array of photonic crystal microcavities uniquely support one or more resonance modes comprising one or more unique resonant frequencies trapped by the array of photonic crystal microcavities resulting in unique minima in a transmission spectrum of the one or more guided modes of the broadband source at the corresponding resonant frequencies of the one or more optical microcavities; and wherein one or more label-free analytes selectively bind to the one or more target binding molecules resulting in shifting the one or more resonant frequencies of the one or more optical microcavities and hence the unique minima in the transmission spectrum of the one or more guided modes of the broadband source.

2. The apparatus of claim 1, further comprising one or more additional target binding molecules selectively bound to the one or more label-free analytes to form a sandwich in which the analyte is held between the one or more target binding molecules and the one or more additional target binding molecules resulting in an additional shift in the resonance frequencies of the one or more optical microcavities and hence the minima in the transmission spectrum of the one or more guided modes of the broadband source.

3. The apparatus of claim 1, further comprising one or more optical microcavities mirrored or duplicated directly across the photonic crystal waveguide.

4. The apparatus of claim 1, wherein the input impedance taper comprises first p pairs of void columnar members across the core immediately adjacent both sides of the core from the input side separated by the width of the core plus 2x times α, where x ranges from z to 0 in decrements of (x times α)/p, where p is a number greater than 5 and z is a fractional number between 0 and 1; and wherein the output impedance taper comprises first p pairs of void columnar members across the core immediately adjacent both sides of the core from the output side separated by the width of the core plus 2x times α, where x ranges from z to 0 in decrements of (x times α)/p, where p is a number greater than 5 and z is a fractional number between 0 and 1.

5. The apparatus of claim 1, wherein the input impedance taper comprises first p pairs of void columnar members across the core immediately adjacent both sides of the core from the input side separated by the width of the core plus 2x times α, where x ranges from z to 0 in decrements of (x times α)/p, where p is a number greater than 5 and z is a fractional number between −1 and 0; and wherein the output impedance taper comprises first p pairs of void columnar members across the core immediately adjacent both sides of the core from the output side separated by the width of the core plus 2x times α, where x ranges from z to 0 in decrements of (x times α)/p, where p is a number greater than 5 and z is a fractional number between −1 and 0.

6. The apparatus of claim 1, the apparatus further configured with tuned frequencies of the one or more guided modes, wherein the frequencies of the one or more guided modes are tuned by changing at least one of: the diameter of the void columnar members, the spacing of the void columnar members, the width of the slab, and the thickness of the slab.

7. The apparatus of claim 1 wherein the width of the photonic crystal waveguide ranges from 0.5 times sqrt(3) times α to 50 times sqrt(3) times α.

8. The apparatus of claim 1, wherein the material of the slab is selected from the group consisting of: silicon, germanium, carbon, gallium nitride, gallium arsenide, gallium phosphide, indium nitride, indium phosphide, indium arsenide, zinc oxide, silicon oxide, silicon nitride, alloys thereof, and organic polymers.

9. The apparatus of claim 1, further comprising a plurality of void columnar members filled with material selected from the group consisting of: air, silicon oxide, silicon nitride, and organic polymers, and wherein the material selected for filling the plurality of void columnar members is different than the material of the slab.

10. The apparatus of claim 1, further comprising each of the one or more optical microcavities of the array of photonic crystal microcavities coated with different target binding molecules.

11. The apparatus of claim 1, further comprising one or more microfluidic channels arrayed orthogonal to the photonic crystal waveguide and parallel to the slab to eliminate cross-contamination between the one or more target binding molecules.

12. The apparatus of claim 1, further comprising the one or more target binding molecules preserved in an aqueous phase.

13. The apparatus of claim 1, wherein the one or more target binding molecules comprise proteins, deoxyribonucleic acid, ribonucleic acid, small molecules, genes, nucleic acids, antigens, or antibodies, each of which shows a specific response to its specific conjugate antigen in blood, serum, saliva or animal fluid.

14. The apparatus of claim 1, wherein the one or more target binding molecules change refractive index with a change in ambient conditions including but not limited to temperature, pressure, humidity, presence of trace gases (greenhouse and non-greenhouse), groundwater contaminants (organic/inorganic, volatile/non-volatile), and pesticides.

15. The apparatus of claim 2, wherein the one or more target binding molecules coated on the array of photonic crystal microcavities are regenerated by removing the bound one or more label-free analytes and the bound one or more additional target binding molecules.

* * * * *